US006194168B1

(12) United States Patent
Gentz et al.

(10) Patent No.: US 6,194,168 B1
(45) Date of Patent: Feb. 27, 2001

(54) EXPRESSION CONTROL SEQUENCES

(75) Inventors: Reiner L. Gentz, Silver Spring; Timothy A. Coleman, Gaithersburg, both of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/044,796

(22) Filed: Mar. 20, 1998

Related U.S. Application Data

(63) Continuation-in-part of application No. 08/941,020, filed on Sep. 30, 1997, now abandoned.

(51) Int. Cl.[7] .............................. C12P 21/02; C12N 1/00; C12N 5/10; C12N 15/11; C12N 15/63
(52) U.S. Cl. ............ 435/69.1; 435/243; 435/320.1; 435/325; 435/410; 536/24.1
(58) Field of Search .............. 536/24.1; 435/320.1, 435/325, 410, 243, 69.1

(56) References Cited

U.S. PATENT DOCUMENTS

| | | | |
|---|---|---|---|
| 4,689,406 | * | 8/1987 | Banks et al. ............... 536/24.1 |
| 4,868,111 | * | 9/1989 | Bujard et al. ............... 435/69.1 |
| 5,362,646 | * | 11/1994 | Bujard et al. ............... 435/252.33 |
| 5,629,205 | * | 5/1997 | Lagosky ..................... 435/320.1 |

OTHER PUBLICATIONS

Roberts et al., PNAS (USA), vol. 76, No. 2, pp. 760–764, Feb. 1979.*
Hawley et al., Nucleic Acids Research, vol. 11, No. 8, pp. 2237–2255, 1983.*
McClure, *Annual Review of Biochemistry*, 54:171–204 (1985).
Horii et al., *Cell*, 27(2):515–522 (Dec., 1981).
Siebenlist et al., *Cell*, 20:269–281 (Jun., 1980).
International Search Report mailed on Feb. 3, 1999, in copending International Application No. PCT/US98/20075.

* cited by examiner

*Primary Examiner*—Terry McKelvey
(74) *Attorney, Agent, or Firm*—Human Genome Sciences, Inc.

(57) ABSTRACT

Expression control sequences are provided for the expression of proteins from a gene of interest. The gene may express viral, prokaryotic, or eukaryotic proteins. These control sequences are produced by combining phage promoter and operator/repressor systems. Expression vectors containing such expression control sequences, microorganisms transformed with such expression vectors and methods for producing viral, prokaryotic, and eukaryotic proteins using the expression control sequences, expression vectors and transformed microorganisms are also provided.

43 Claims, 8 Drawing Sheets

Expression Control Sequence: M

```
                          -30              -12
TAAAAAACTGCAAAAAATAGTTTGACTTGTGAGCGGATAACAATTAAGATGTACCCAGT
TCG
```

Expression Control Sequence: M+D

```
                          -30              -12
TAAAAAACTGCAAAAAATAGTTTGACTTGTGAGCGGATAACAATTAAGATGTACCCAGTGT
GAGCGGATAACAATT
```

Expression Control Sequence: U+D

```
                   -30              -12
TTGTGAGCGGATAACAATTTGACACCCTAGCCGATAGGCTTTAAGATGTACCCAGTGTG

AGCGGATAACAATT
```

Expression Control Sequence: M+D1

```
                                -30              -12
GATCCAAGCTTAAAAAACTGCAAAAAATAGTTTGACTTGTGAGCGGATAACAATTAAGAT

GTACCCAATTGTGAGCGGATAACAATTTCACACATTAAAGAGGAGAAATTACATATG
```

Expression Control Sequence: M+D2

```
                                -30              -12
GATCCAAGCTTAAAAAACTGCAAAAAATAGTTTGACTTGTGAGCGGATAACAATTAAGAT

GTACCCAGTGTGAGCGGATAACAATTTCACATTAAAGAGGAGAAATTACATATG
```

FIG.1

```
           HinD III
         AAGCTTAAAAAACTGCAAAAAATAGTTTGACTTGTGAGCGGATAACAATTAAGATGTACCCAATTGTGAGCGGATAACAA
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖ 80
         TTCGAATTTTTTGACGTTTTTTATCAAACTGAACACTCGCCTATTGTTAATTCTACATGGGTTAACACTCGCCTATTGTT
                                    ┌──▶┤        ├──▶           ├──────┐
                                    └-30┴──Operator 1──┴-12┘     └──Operator 2──┘
                         Nde I
         TTTCACACATTAAAGAGGAGAAATTACATATGGACCGTTTCCACGCTACCTCCGCTGACTGCTGCATCTCCTACACCCCG
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖ 160
         AAAGTGTGTAATTTCTCCTCTTTAATGTATACCTGGCAAAGGTGCGATGGAGGCGACTGACGACGTAGAGGATGTGGGGC
         ┘       ├─S/D─┤     Met Asp Arg Phe His Ala Thr Ser Ala Asp Cys Cys Ile Ser Tyr Thr Pro
                                └──────────────────── MPIF-1 ────────────────────

CGTTCCATCCCGTGCTCGCTGCTGGAATCCTACTTCGAAACCAACTCCGAATGCTCCAAACCGGGTGTTATCTTCCTGAC
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖ 240
         GCAAGGTAGGGCACGAGCGACGACCTTAGGATGAAGCTTTGGTTGAGGCTTACGAGGTTTGGCCCACAATAGAAGGACTG
         Arg Ser Ile Pro Cys Ser Leu Leu Glu Ser Tyr Phe Glu Thr Asn Ser Glu Cys Ser Lys Pro Gly Val Ile Phe Leu Thr
         ──────────────────────────── MPIF-1 ────────────────────────────

CAAAAAAGGTCGTCGTTTCTGCGCTAACCCGTCCGACAAACAGGTTCAGGTTTGTATGCGTATGCTGAAACTGGACACCC
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖ 320
         GTTTTTTCCAGCAGCAAAGACGCGATTGGGCAGGCTGTTTGTCCAAGTCCAAACATACGCATACGACTTTGACCTGTGGG
         Lys Lys Gly Arg Arg Phe Cys Ala Asn Pro Ser Asp Lys Gln Val Gln Val Cys Met Arg Met Leu Lys Leu Asp Thr
         ──────────────────────────── MPIF-1 ────────────────────────────

EcoR I
         GTATCAAAACCCGTAAAAACTGATAAGGTACCTAAGTGAGTAGGGCGTCCGATCGACGGACGCCTTTTTTTTGAATTCGT
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖ 400
         CATAGTTTTGGGCATTTTTGACTATTCCATGGATTCACTCATCCCGCAGGCTAGCTGCCTGCGGAAAAAAAACTTAAGCA
         Arg Ile Lys Thr Arg Lys Asn                ├─────────────────┤
         ──── MPIF-1 ────────┘                      └── Tsc Terminator ──┘

AATCATGGTCATAGCTGTTTCCTGTGTGAAATTGTTATCCGCTCACAATTCCACACAACATACGAGCCCGGAAGCATAAAG
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖ 480
         TTAGTACCAGTATCGACAAAGGACACACTTTAACAATAGGCGAGTGTTAAGGTGTGTTGTATGCTCGGCCTTCGTATTTC

TGTAAAGCCTGGGGTGCCTAATGAGTGAGCTAACTCACATTAATTGCGTTGCGCTCACTGCCCGCTTTCCAGTCGGGAAA
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖ 560
         ACATTTCGGACCCCACGGATTACTCACTCGATTGAGTGTAATTAACGCAACGCGAGTGACGGGCGAAAGGTCAGCCCTTT
```

FIG.2A

```
                Pvu II
CCTGTCGTGCCAGCTGCATTAATGAATCGGCCAACGCGCGGGGAGAGGCGGTTTGCGTATTGGGCGCTCTTCCGCTTCCT
++++++++|++++++++|++++++++|++++++++|++++++++|++++++++|++++++++|++++++++| 640
GGACAGCACGGTCGACGTAATTACTTAGCCGGTTGCGCGCCCCTCTCCGCCAAACGCATAACCCGCGAGAAGGCGAAGGA

CGCTCACTGACTCGCTGCGCTCGGTCGTTCGGCTGCGGCGAGCGGTATCAGCTCACTCAAAGGCGGTAATACGGTTATCC
++++++++|++++++++|++++++++|++++++++|++++++++|++++++++|++++++++|++++++++| 720
GCGAGTGACTGAGCGACGCGAGCCAGCAAGCCGACGCCGCTCGCCATAGTCGAGTGAGTTTCCGCCATTATGCCAATAGG

ACAGAATCAGGGGATAACGCAGGAAAGAACATGTGAGCAAAAGGCCAGCAAAAGGCCAGGAACCGTAAAAAGGccGcGrT
++++++++|++++++++|++++++++|++++++++|++++++++|++++++++|++++++++|++++++++| 800
TGTCTTAGTCCCCTATTGCGTCCTTTCTTGTACACTCGTTTTCCGGTCGTTTTCCGGTCCTTGGCATTTTTCCGGCGCAA

GCTGGCGTTTTTCCATAGGCTCCGCCCCCCTGACGAGCATCACAAAAATCGACGCTCAAGTCAGAGGTGGCGAAACCCGA
++++++++|++++++++|++++++++|++++++++|++++++++|++++++++|++++++++|++++++++| 880
CGACCGCAAAAAGGTATCCGAGGCGGGGGGACTGCTCGTAGTGTTTTTAGCTGCGAGTTCAGTCTCCACCGCTTTGGGCT

CAGGACTATAAAGATACCAGGCGTTTCCCCCTGGAAGCTCCCTCGTGCGCTCTCCTGTTCCGACCCTGCCGCTTACCGGA
++++++++|++++++++|++++++++|++++++++|++++++++|++++++++|++++++++|++++++++| 960
GTCCTGATATTTCTATGGTCCGCAAAGGGGGACCTTCGAGGGAGCACGCGAGAGGACAAGGCTGGGACGGCGAATGGCCT

TACCTGTCCGCCTTTCTCCCTTCGGGAAGCGTGGCGCTTTCTCATAGCTCACGCTGTAGGTATCTCAGTTCGGTGTAGGT
++++++++|++++++++|++++++++|++++++++|++++++++|++++++++|++++++++|++++++++| 1040
ATGGACAGGCGGAAAGAGGGAAGCCCTTCGCACCGCGAAAGAGTATCGAGTGCGACATCCATAGAGTCAAGCCACATCCA
                                    ⌐────── oriC ──────┐
CGTTCGCTCCAAGCTGGGCTGTGTGCACGAACCCCCCGTTCAGCCCGACCGCTGCGCCTTATCCGGTAACTATCGTCTTG
++++++++|++++++++|++++++++|++++++++|++++++++|++++++++|++++++++|++++++++| 1120
GCAAGCGAGGTTCGACCCGACACACGTGCTTGGGGGGCAAGTCGGGCTGGCGACGCGGAATAGGCCATTGATAGCAGAAC AGTCCAACCCGGTAAGACACGACTTATCGCCACTGGCAGCAGCCACTGGTAACAGGATTAGCAGAGCGAGGTATGTAGGC
++++++++|++++++++|++++++++|++++++++|++++++++|++++++++|++++++++|++++++++| 1200
TCAGGTTGGGCCATTCTGTGCTGAATAGCGGTGACCGTCGTCGGTGACCATTGTCCTAATCGTCTCGCTCCATACATCCG GGTGCTACAGAGTTCTTGAAGTGGTGGCCTAACTACGGCTACACTAGAAGAACAGTATTTGGTATCTGCGCTCTGCTGAA
++++++++|++++++++|++++++++|++++++++|++++++++|++++++++|++++++++|++++++++| 1280
CCACGATGTCTCAAGAACTTCACCACCGGATTGATGCCGATGTGATCTTCTTGTCATAAACCATAGACGCGAGACGACTT GCCAGTTACCTTCGGAAAAAGAGTTGGTAGCTCTTGATCCGGCAAACAAACCACCGCTGGTAGCGGTGGTTTTTTTGTTT
++++++++|++++++++|++++++++|++++++++|++++++++|++++++++|++++++++|++++++++| 1360
CGGTCAATGGAAGCCTTTTTCTCAACCATCGAGAACTAGGCCGTTTGTTTGGTGGCGACCATCGCCACCAAAAAAACAAA GCAAGCAGCAGATTACGCGCAGAAAAAAAGGATCTCAAGAAGATCCTTTGATCTTTTCTACGGGGTCTGACGCTCAGTGG
++++++++|++++++++|++++++++|++++++++|++++++++|++++++++|++++++++|++++++++| 1440
CGTTCGTCGTCTAATGCGCGTCTTTTTTTCCTAGAGTTCTTCTAGGAAACTAGAAAAGATGCCCCAGACTGCGAGTCACC
```

FIG.2B

```
                                        Sal I
AACGAAAACTCACGTTAAGGGATTTTGGTCATGAGATTATCGTCGACAATTCGCGCGCGAAGGCGAAGCGGCATGCATTT
++++++++|++++++++|++++++++|++++++++|++++++++|++++++++|++++++++|++++++++|++++++++| 1520
TTGCTTTTGAGTGCAATTCCCTAAAACCAGTACTCTAATAGCAGCTGTTAAGCGCGCGCTTCCGCTTCGCCGTACGTAAA

ACGTTGACACCATCGAATGGTGCAAAACCTTTCGCGGTATGGCATGATAGCGCCCGGAAGAGAGTCAATTCAGGGTGGTG
++++++++|++++++++|++++++++|++++++++|++++++++|++++++++|++++++++|++++++++|++++++++| 1600
TGCAACTGTGGTAGCTTACCACGTTTTGGAAAGCGCCATACCGTACTATCGCGGGCCTTCTCTCAGTTAAGTCCCACCAC

AATGTGAAACCAGTAACGTTATACGATGTCGCAGAGTATGCCGGTGTCTCTTATCAGACCGTTTCCCGCGTGGTGAACCA
++++++++|++++++++|++++++++|++++++++|++++++++|++++++++|++++++++|++++++++|++++++++| 1680
TTACACTTTGGTCATTGCAATATGCTACAGCGTCTCATACGGCCACAGAGAATAGTCTGGCAAAGGGCGCACCACTTGGT

GGCCAGCCACGTTTCTGCGAAAACGCGGGAAAAAGTGGAAGCGGCGATGGCGGAGCTGAATTACATTCCCAACCGCGTGG
++++++++|++++++++|++++++++|++++++++|++++++++|++++++++|++++++++|++++++++|++++++++| 1760
CCGGTCGGTGCAAAGACGCTTTTGCGCCCTTTTTCACCTTCGCCGCTACCGCCTCGACTTAATGTAAGGGTTGGCGCACC
                                                Met Ala Glu Leu Asn Tyr Ile Pro Asn Arg Val
                                                |——————— Lac I ———————

CACAACAACTGGCGGGCAAACAGTCGTTGCTGATTGGCGTTGCCACCTCCAGTCTGGCCCTGCACGCGCCGTCGCAAATT
++++++++|++++++++|++++++++|++++++++|++++++++|++++++++|++++++++|++++++++|++++++++| 1840
GTGTTGTTGACCGCCCGTTTGTCAGCAACGACTAACCGCAACGGTGGAGGTCAGACCGGGACGTGCGCGGCAGCGTTTAA
Ala Gln Gln Leu Ala Gly Lys Gln Ser Leu Leu Ile Gly Val Ala Thr Ser Ser Leu Ala Leu His Ala Pro Ser Gln Ile
——————————————————————— Lac I ———————————————————————

GTCGCGGCGATTAAATCTCGCGCCGATCAACTGGGTGCCAGCGTGGTGGTGTCGATGGTAGAACGAAGCGGCGTCGAAGC
++++++++|++++++++|++++++++|++++++++|++++++++|++++++++|++++++++|++++++++|++++++++| 1920
CAGCGCCGCTAATTTAGAGCGCGGCTAGTTGACCCACGGTCGCACCACCACAGCTACCATCTTGCTTCGCCGCAGCTTCG
Val Ala Ala Ile Lys Ser Arg Ala Asp Gln Leu Gly Ala Ser Val Val Val Ser Met Val Glu Arg Ser Gly Val Glu Ala
——————————————————————— Lac I ———————————————————————

CTGTAAAGCGGCCGGTGCACAATCTTCTCGCGCAACGCGTCAGTGGGCTGATCATTAACTATCCGCTGGATGACCAGGATG
++++++++|++++++++|++++++++|++++++++|++++++++|++++++++|++++++++|++++++++|++++++++| 2000
GACATTTCGCCGGCCACGTGTTAGAAGAGCGCGTTGCGCAGTCACCCGACTAGTAATTGATAGGCGACCTACTGGTCCTAC
Cys Lys Ala Ala Val His Asn Leu Leu Ala Gln Arg Val Ser Gly Leu Ile Ile Asn Tyr Pro Leu Asp Asp Gln Asp
——————————————————————— Lac I ———————————————————————

CCATTGCTGTGGAAGCTGCCTGCACTAATGTTCCGGCGTTATTTCTTGATGTCTCTGACCAGACACCCATCAACAGTATT
++++++++|++++++++|++++++++|++++++++|++++++++|++++++++|++++++++|++++++++|++++++++| 2080
GGTAACGACACCTTCGACGGACGTGATTACAAGGCCGCAATAAAGAACTACAGAGACTGGTCTGTGGGTAGTTGTCATAA
Ala Ile Ala Val Glu Ala Ala Cys Thr Asn Val Pro Ala Leu Phe Leu Asp Val Ser Asp Gln Thr Pro Ile Asn Ser Ile
——————————————————————— Lac I ———————————————————————
```

FIG.2C

```
ATTTTCTCCCATGAAGACGGTACGCGACTGGGCGTGGAGCATCTGGTCGCATTGGGTCACCAGCAAATCGCGCTGTTAGC
++++++++|++++++++|++++++++|++++++++|++++++++|++++++++|++++++++|++++++++|++++++++| 2160
TAAAAGAGGGTACTTCTGCCATGCGCTGACCCGCACCTCGTAGACCAGCGTAACCCAGTGGTCGTTTAGCGCGACAATCG
 Ile Phe Ser His Glu Asp Gly Thr Arg Leu Gly Val Glu His Leu Val Ala Leu Gly His Gln Gln Ile Ala Leu Leu Ala
                                              ———————— Lac I ————————
═══════════════════════════════════════════════════════════════════════════════════

GGGCCCATTAAGTTCTGTCTCGGCGCGTCTGCGTCTGGCTGGCTGGCATAAATATCTCACTCGCAATCAAATTCAGCCGA
++++++++|++++++++|++++++++|++++++++|++++++++|++++++++|++++++++|++++++++|++++++++| 2240
CCCGGGTAATTCAAGACAGAGCCGCGCAGACGCAGACCGACCGACCGTATTTATAGAGTGAGCGTTAGTTTAAGTCGGCT
 Gly Pro Leu Ser Ser Val Ser Ala Arg Leu Arg Leu Ala Gly Trp His Lys Tyr Leu Thr Arg Asn Gln Ile Gln Pro
                                              ———————— Lac I ————————
═══════════════════════════════════════════════════════════════════════════════════

TAGCGGAACGGGAAGGCGACTGGAGTGCCATGTCCGGTTTTCAACAAACCATGCAAATGCTGAATGAGGGCATCGTTCCC
++++++++|++++++++|++++++++|++++++++|++++++++|++++++++|++++++++|++++++++|++++++++| 2320
ATCGCCTTGCCCTTCCGCTGACCTCACGGTACAGGCCAAAAGTTGTTTGGTACGTTTACGACTTACTCCCGTAGCAAGGG
 Ile Ala Glu Arg Glu Gly Asp Trp Ser Ala Met Ser Gly Phe Gln Gln Thr Met Gln Met Leu Asn Glu Gly Ile Val Pro
                                              ———————— Lac I ————————
═══════════════════════════════════════════════════════════════════════════════════

ACTGCGATGCTGGTTGCCAACGATCAGATGGCGCTGGGCGCAATGCGCGCCATTACCGAGTCCGGGCTGCGCGTTGGTGC
++++++++|++++++++|++++++++|++++++++|++++++++|++++++++|++++++++|++++++++|++++++++| 2400
TGACGCTACGACCAACGGTTGCTAGTCTACCGCGACCCGCGTTACGCGCGGTAATGGCTCAGGCCCGACGCGCAACCACG
 Thr Ala Met Leu Val Ala Asn Asp Gln Met Ala Leu Gly Ala Met Arg Ala Ile Thr Glu Ser Gly Leu Arg Val Gly Ala
                                              ———————— Lac I ————————
═══════════════════════════════════════════════════════════════════════════════════

GGATATCTCGGTAGTGGGATACGACGATACCGAAGACAGCTCATGTTATATCCCGCCGTTAACCACCATCAAACAGGATT
++++++++|++++++++|++++++++|++++++++|++++++++|++++++++|++++++++|++++++++|++++++++| 2480
CCTATAGAGCCATCACCCTATGCTGCTATGGCTTCTGTCGAGTACAATATAGGGCGGCAATTGGTGGTAGTTTGTCCTAA
 Asp Ile Ser Val Val Gly Tyr Asp Asp Thr Glu Asp Ser Ser Cys Tyr Ile Pro Pro Leu Thr Thr Ile Lys Gln Asp
                                              ———————— Lac I ————————
═══════════════════════════════════════════════════════════════════════════════════

Pvu II
                                                                           |
TTCGCCTGCTGGGGCAAACCAGCGTGGACCGCTTGCTGCAACTCTCTCAGGGCCAGGCCGGTGAAGGGCAATCAGCTGTTG
++++++++|++++++++|++++++++|++++++++|++++++++|++++++++|++++++++|++++++++|++++++++| 2560
AAGCGGACGACCCCGTTTGGTCGCACCTGGCGAACGACGTTGAGAGAGTCCCGGTCCGCCACTTCCCGTTAGTCGACAAC
 Phe Arg Leu Leu Gly Gln Thr Ser Val Asp Arg Leu Leu Gln Leu Ser Gln Gly Gln Ala Val Lys Gly Asn Gln Leu Leu
                                              ———————— Lac I ————————
═══════════════════════════════════════════════════════════════════════════════════

CCCGTCTCACTGGTGAAAAGAAAAACCACCCTGGCGCCCAATACGCAAACCGCCTCTCCCCGCGCGTTGGCCGATTCATT
++++++++|++++++++|++++++++|++++++++|++++++++|++++++++|++++++++|++++++++|++++++++| 2640
GGGCAGAGTGACCACTTTTCTTTTTGGTGGGACCGCGGGTTATGCGTTTGGCGGAGAGGGGCGCGCAACCGGCTAAGTAA
 Pro Val Ser Leu Val Lys Arg Lys Thr Thr Leu Ala Pro Asn Thr Gln Thr Ala Ser Pro Arg Ala Leu Ala Asp Ser Leu
                                              ———————— Lac I ————————
═══════════════════════════════════════════════════════════════════════════════════
```

FIG.2D

```
                Pvu II                                                                  Sal I
        AATGCAGCTGGCACGACAGGTTTCCCGACTGGAAAGCGGGCAGTGAGCGCAACGCAATTAATGTAAGTTAGCGCGAATTG
        ||||||||||||||||||||||||||||||||||||||||||||||||||||||||||||||||||||||||||||||||  2720
        TTACGTCGACCGTGCTGTCCAAAGGGCTGACCTTTCGCCCGTCACTCGCGTTGCGTTAATTACATTCAATCGCGCTTAAC
        Met Gln Leu Ala Arg Gln Val Ser Arg Leu Glu Ser Gly Gln
        ─────────── Lac I ───────────────────▶

Pst I
        TCGACCAAAGCGGCCATCGTGCCTCCCCACTCCTGCAGTTCGGGGGCATGGATGCGCGGATAGCCGCTGCTGGTTTCCTG
        ||||||||||||||||||||||||||||||||||||||||||||||||||||||||||||||||||||||||||||||||  2800
        AGCTGGTTTCGCCGGTAGCACGGAGGGGTGAGGACGTCAAGCCCCCGTACCTACGCGCCTATCGGCGACGACCAAAGGAC

Pvu II
        GATGCCGACGGATTTGCACTGCCGGTAGAACTCCGCGAGGTCGTCCAGCCTCAGGCAGCAGCTGAACCAACTCGCGAGGG
        ||||||||||||||||||||||||||||||||||||||||||||||||||||||||||||||||||||||||||||||||  2880
        CTACGGCTGCCTAAACGTGACGGCCATCTTGAGGCGCTCCAGCAGGTCGGAGTCCGTCGTCGACTTGGTTGAGCGCTCCC

GATCGAGCCCGGGGTGGGCGAAGAACTCCAGCATGAGATCCCCGCGCTGGAGGATCATCCAGCCGGCGTCCCGGAAAACG
        ||||||||||||||||||||||||||||||||||||||||||||||||||||||||||||||||||||||||||||||||  2960
        CTAGCTCGGGCCCCACCCGCTTCTTGAGGTCGTACTCTAGGGGCGCGACCTCCTAGTAGGTCGGCCGCAGGGCCTTTTGC

ATTCCGAAGCCCAACCTTTCATAGAAGGCGGCGGTGGAATCGAAATCTCGTGATGGCAGGTTGGGCGTCGCTTGGTCGGT
        ||||||||||||||||||||||||||||||||||||||||||||||||||||||||||||||||||||||||||||||||  3040
        TAAGGCTTCGGGTTGGAAAGTATCTTCCGCCGCCACCTTAGCTTTAGAGCACTACCGTCCAACCCGCAGCGAACCAGCCA

CATTTCGAACCCCAGAGTCCCGCTCAGAAGAACTCGTCAAGAAGGCGATAGAAGGCGATGCGCTGCGAATCGGGAGCGGC
        ||||||||||||||||||||||||||||||||||||||||||||||||||||||||||||||||||||||||||||||||  3120
        GTAAAGCTTGGGGTCTCAGGGCGAGTCTTCTTGAGCAGTTCTTCCGCTATCTTCCGCTACGCGACGCTTAGCCCTCGCCG
                        ◀──────────────────────────────────────────────
                        Phe Phe Glu Asp Leu Leu Arg Tyr Phe Ala Ile Arg Gln Ser Asp Pro Ala Ala
                        └─────────────────────── kan ──────────────────

GATACCGTAAAGCACGAGGAAGCGGTCAGCCCATTCGCCGCCAAGCTCTTCAGCAATATCACGGGTAGCCAACGCTATGT
        ||||||||||||||||||||||||||||||||||||||||||||||||||||||||||||||||||||||||||||||||  3200
        CTATGGCATTTCGTGCTCCTTCGCCAGTCGGGTAAGCGGCGGTTCGAGAAGTCGTTATAGTGCCCATCGGTTGCGATACA
        ━━━━━━━━━━━━━━━━━━━━━━━━━━━━━━━━━━━━━━━━━━━━━━━━━━━━━━━━━━━━━━━━━━━━━━━━━━━━━━━━
        Ile Gly Tyr Leu Val Leu Phe Arg Asp Ala Trp Glu Gly Gly Leu Glu Glu Ala Ile Asp Arg Thr Ala Leu Ala Ile Asp
        ─────────────────────────────── kan ──────────────

CCTGATAGCGGTCCGCCACACCCAGCCGGCCACAGTCGATGAATCCAGAAAAGCGGCCATTTTCCACCATGATATTCGGC
        ||||||||||||||||||||||||||||||||||||||||||||||||||||||||||||||||||||||||||||||||  3280
        GGACTATCGCCAGGCGGTGTGGGTCGGCCGGTGTCAGCTACTTAGGTCTTTTCGCCGGTAAAAGGTGGTACTATAAGCCG
        ━━━━━━━━━━━━━━━━━━━━━━━━━━━━━━━━━━━━━━━━━━━━━━━━━━━━━━━━━━━━━━━━━━━━━━━━━━━━━━━━
        Gln Tyr Arg Asp Ala Val Gly Leu Arg Gly Cys Asp Ile Phe Gly Ser Phe Arg Gly Asn Glu Val Met Ile Asn Pro
        ─────────────────────────────── kan ──────────────
```

FIG. 2E

```
AAGCAGGCATCGCCATGGGTCACGACGAGATCCTCGCCGTCGGGCATGCGCGCCTTGAGCCTGGCGAACAGTTCGGCTGG
||||||||||||||||||||||||||||||||||||||||||||||||||||||||||||||||||||||||||||||||  3360
TTCGTCCGTAGCGGTACCCAGTGCTGCTCTAGGAGCGGCAGCCCGTACGCGCGGAACTCGGACCGCTTGTCAAGCCGACC
```

Leu Cys Ala Asp Gly His Thr Val Val Leu Asp Glu Gly Asp Pro Met Arg Ala Lys Leu Arg Ala Phe Leu Glu Ala Pro
——————————————————————— kan ———————————

```
CGCGAGCCCCTGATGCTCTTCGTCCAGATCATCCTGATCGACAAGACCGGCTTCCATCCGAGTACGTGCTCGCTCGATGC
||||||||||||||||||||||||||||||||||||||||||||||||||||||||||||||||||||||||||||||||  3440
GCGCTCGGGGACTACGAGAAGCAGGTCTAGTAGGACTAGCTGTTCTGGCCGAAGGTAGGCTCATGCACGAGCGAGCTACG
```

Ala Leu Gly Gln His Glu Glu Asp Leu Asp Asp Gln Asp Val Leu Gly Ala Glu Met Arg Thr Arg Ala Arg Glu Ile Arg
——————————————————————— kan ———————————

```
GATGTTTCGCTTGGTGGTCGAATGGGCAGGTAGCCGGATCAAGCGTATGCAGCCGCCGCATTGCATCAGCCATGATGGAT
||||||||||||||||||||||||||||||||||||||||||||||||||||||||||||||||||||||||||||||||  3520
CTACAAAGCGAACCACCAGCTTACCCGTCCATCGGCCTAGTTCGCATACGTCGGCGGCGTAACGTAGTCGGTACTACCTA
```

His Lys Ala Gln His Asp Phe Pro Cys Thr Ala Pro Asp Leu Thr His Leu Arg Arg Met Ala Asp Ala Met Ile Ser
——————————————————————— kan ———————————

```
ACTTTCTCGGCAGGAGCAAGGTGAGATGACAGGAGATCCTGCCCCGGCACTTCGCCCAATAGCAGCCAGTCCCTTCCCGC
||||||||||||||||||||||||||||||||||||||||||||||||||||||||||||||||||||||||||||||||  3600
TGAAAGAGCCGTCCTCGTTCCACTCTACTGTCCTCTAGGACGGGGCCGTGAAGCGGGTTATCGTCGGTCAGGGAAGGGCG
```

Val Lys Glu Ala Pro Ala Leu His Ser Ser Leu Leu Asp Gln Gly Pro Val Glu Gly Leu Leu Leu Trp Asp Arg Gly Ala
——————————————————————— kan ———————————

Pvu II                                                                      Pst I
```
TTCAGTGACAACGTCGAGCACAGCTGCGCAAGGAACGCCCGTCGTGGCCAGCCACGATAGCCGCGCTGCCTCGTCCTGCA
||||||||||||||||||||||||||||||||||||||||||||||||||||||||||||||||||||||||||||||||  3680
AAGTCACTGTTGCAGCTCGTGTCGACGCGTTCCTTGCGGGCAGCACCGGTCGGTGCTATCGGCGCGACGGAGCAGGACGT
```

Glu Thr Val Val Asp Leu Val Ala Ala Cys Pro Val Gly Thr Thr Ala Leu Trp Ser Leu Arg Ala Ala Glu Asp Gln Leu
——————————————————————— kan ———————————

```
GTTCATTCAGGGCACCGGACAGGTCGGTCTTGACAAAAAGAACCGGGCGCCCCTGCGCTGACAGCCGGAACACGGCGGCA
||||||||||||||||||||||||||||||||||||||||||||||||||||||||||||||||||||||||||||||||  3760
CAAGTAAGTCCCGTGGCCTGTCCAGCCAGAACTGTTTTTCTTGGCCCGCGGGGACGCGACTGTCGGCCTTGTGCCGCCGT
```

Glu Asn Leu Ala Gly Ser Leu Asp Thr Lys Val Phe Leu Val Pro Arg Gly Gln Ala Ser Leu Arg Phe Val Ala Ala
——————————————————————— kan ———————————

FIG.2F

```
TCAGAGCAGCCGATIGTCTGTTGTGCCCAGTCATAGCCGAATAGCCTCTCCACCCAAGCGGCCGGAGAACCTGCCGTGCAA
++++++++|++++++++|++++++++|++++++++|++++++++|++++++++|++++++++|++++++++|++++++++|++++++++| 3840
AGTCTCGTCGGCTAACAGACAACACGGGTCAGTATCGCCTTATCGGACAGGTCCGTTCGCCGGCCTCTTGGACGCACGTT
```

Asp Ser Cys Gly Ile Thr Gln Gln Ala Trp Asp Tyr Gly Phe Leu Arg Glu Val Trp Ala Ala Pro Ser Gly Ala His Leu
———————————————————————— kan ————————————————————————

```
                                              Bgl II
TCCATCTTGTTCAATCATGCGAAACGATCCTCATCCTGTCTCTTGATCAGATCTTGATCCCCTGCGCCATCAGATCCTTG
++++++++|++++++++|++++++++|++++++++|++++++++|++++++++|++++++++|++++++++|++++++++|++++++++| 3840
AGGTAGAACAAGTTAGTACGCTTTGCTAGGAGTAGGACAGAGAACTAGTCTAGAACTAGGGGACGCGGTAGTCTAGGAAC
```

Gly Asp Gln Glu Ile Met
———— kan ————

```
                                                              Pvu II
GCGGCAAGAAAGCCATCCAGTTTACTTTGCAGGGCTTCCCAACCTTACCAGAGGGCGCCCCAGCTGGCAATTCCGGTTCG
++++++++|++++++++|++++++++|++++++++|++++++++|++++++++|++++++++|++++++++|++++++++|++++++++| 4000
CGCCGTTCTTTCGGTAGGTCAAATGAAACGTCCCGAAGGGTTGGAATGGTCTCCCGCGGGGTCGACCGTTAAGGCCAAGC

CTTGCTGTCCATAAAACCGCCCAGTCTAGCTATCGCCATGTAAGCCCACTGCAAGCTACCTGCTTTCTCTTTGCGCTTGC
++++++++|++++++++|++++++++|++++++++|++++++++|++++++++|++++++++|++++++++|++++++++|++++++++| 4080
GAACGACAGGTATTTTGGCGGGTCAGATCGATAGCGGTACATTCGGGTGACGTTCGATGGACGAAAGAGAAACGCGAACG

GTTTTCCCTTGTCCAGATAGCCCAGTAGCTGACATTCATCCGGGGTCAGCACCGTTTCTGCGGACTGGCTTTCTACGTGT
++++++++|++++++++|++++++++|++++++++|++++++++|++++++++|++++++++|++++++++|++++++++|++++++++| 4160
CAAAAGGGAACAGGTCTATCGGGTCATCGACTGTAAGTAGGCCCCAGTCGTGGCAAAGACGCCTGACCGAAAGATGCACA

TCCGCTTCCTTTAGCAGCCCTTGCGCCCTGAGTGCTTGCGGCAGCGTG
++++++++|++++++++|++++++++|++++++++|++++++++|+++++++ 4208
AGGCGAAGGAAATCGTCGGGAACGCGGGACTCACGAACGCCGTCGCAC
```

FIG.2G

SEQUENCE LISTING

<160> NUMBER OF SEQ ID NOS: 14

<210> SEQ ID NO 1
<211> LENGTH: 18
<212> TYPE: DNA
<213> ORGANISM: Homo sapiens

<400> SEQUENCE: 1
attaaagagg agaaatta                                                      18

<210> SEQ ID NO 2
<211> LENGTH: 28
<212> TYPE: DNA
<213> ORGANISM: Homo sapiens

<400> SEQUENCE: 2
aattgtgagc ggataacaat ttcacaca                                           28

<210> SEQ ID NO 3
<211> LENGTH: 16
<212> TYPE: DNA
<213> ORGANISM: Homo sapiens

<400> SEQUENCE: 3
gtgagcggat aacaat                                                        16

<210> SEQ ID NO 4
<211> LENGTH: 62
<212> TYPE: DNA
<213> ORGANISM: Homo sapiens

<400> SEQUENCE: 4
taaaaaactg caaaaaatag tttgacttgt gagcggataa caattaagat gtacccagtt        60
cg                                                                       62

<210> SEQ ID NO 5
<211> LENGTH: 76
<212> TYPE: DNA
<213> ORGANISM: Homo sapiens

<400> SEQUENCE: 5
taaaaaactg caaaaaatag tttgacttgt gagcggataa caattaagat gtacccagtg        60
tgagcggata acaatt                                                        76

<210> SEQ ID NO 6
<211> LENGTH: 73
<212> TYPE: DNA
<213> ORGANISM: Homo sapiens

<400> SEQUENCE: 6
ttgtgagcgg ataacaattt gacaccctag ccgataggct taagatgta cccagtgtga         60 gcggataaca att                                                           73

<210> SEQ ID NO 7
<211> LENGTH: 122
<212> TYPE: DNA
<213> ORGANISM: Homo sapiens

<400> SEQUENCE: 7
gatccaagct taaaaactg caaaaaatag tttgacttgt gagcggataa caattaagat         60

```
gtacccaatt gtgagcggat aacaatttca cacattaaag aggagaaatt acatatggat    120
cg                                                                   122
```

<210> SEQ ID NO 8
<211> LENGTH: 119
<212> TYPE: DNA
<213> ORGANISM: Homo sapiens

<400> SEQUENCE: 8

```
gatccaagct taaaaaactg caaaaaatag tttgacttgt gagcggataa caattaagat     60
gtacccagtg tgagcggata acaatttcac attaaagagg agaaattaca tatggatcg    119
```

<210> SEQ ID NO 9
<211> LENGTH: 4208
<212> TYPE: DNA
<213> ORGANISM: Homo sapiens

<400> SEQUENCE: 9

```
aagcttaaaa aactgcaaaa aatagtttga cttgtgagcg gataacaatt aagatgtacc     60
caattgtgag cggataacaa tttcacacat aaagaggag aaattacata tggaccgttt    120
ccacgctacc tccgctgact gctgcatctc ctacacccg cgttccatcc cgtgctcgct    180
gctggaatcc tacttcgaaa ccaactccga atgctccaaa ccgggtgtta tcttcctgac    240
caaaaaaggt cgtcgtttct cgctaaaccc gtccgacaaa caggttcagg tttgtatgcg    300
tatgctgaaa ctggacaccc gtatcaaaac ccgtaaaaac tgataaggta cctaagtgag    360
tagggcgtcc gatcgacgga cgcctttttt ttgaattcgt aatcatggtc atagctgttt    420
cctgtgtgaa attgttatcc gctcacaatt ccacacaaca tacgagccgg aagcataaag    480
tgtaaagcct ggggtgccta atgagtgagc taactcacat taattgcgtt gcgctcactg    540
cccgctttcc agtcgggaaa cctgtcgtgc cagctgcatt aatgaatcgg ccaacgcgcg    600
gggagaggcg gtttgcgtat tgggcgctct tccgcttcct cgctcactga ctcgctgcgc    660
tcggtcgttc ggctgcggcg agcggtatca gctcactcaa aggcggtaat acggttatcc    720
acagaatcag gggataacgc aggaaagaac atgtgagcaa aaggccagca aaaggccagg    780
aaccgtaaaa aggccgcgtt gctggcgttt ttccataggc tccgccccc tgacgagcat    840 cacaaaaatc gacgctcaag tcagaggtgg cgaaacccga caggactata agataccag    900 gcgtttcccc ctggaagctc cctcgtgcgc tctcctgttc cgaccctgcc gcttaccgga    960
tacctgtccg cctttctccc ttcgggaagc gtggcgcttt ctcatagctc acgctgtagg   1020
tatctcagtt cggtgtaggt cgttcgctcc aagctgggct gtgtgcacga accccccgtt   1080
cagcccgacc gctgcgcctt atccggtaac tatcgtcttg agtccaaccc ggtaagacac   1140
gacttatcgc cactggcagc agccactggt aacaggatta gcagagcgag gtatgtaggc   1200
ggtgctacag agttcttgaa gtggtggcct aactacggct acactagaag aacagtattt   1260
ggtatctgcg ctctgctgaa gccagttacc ttcggaaaaa gagttggtag ctcttgatcc   1320
ggcaaacaaa ccaccgctgg tagcggtggt ttttttgttt gcaagcagca gattacgcgc   1380
agaaaaaaag gatctcaaga agatcctttg atcttttcta cggggtctga cgctcagtgg   1440
aacgaaaact cacgttaagg gattttggtc atgagattat cgtcgacaat tcgcgcgcga   1500
aggcgaagcg gcatgcattt acgttgacac catcgaatgg tgcaaaacct ttcgcggtat   1560
ggcatgatag cgcccggaag agagtcaatt cagggtggtg aatgtgaaac cagtaacgtt   1620
```

-continued

```
atacgatgtc gcagagtatg ccggtgtctc ttatcagacc gtttcccgcg tggtgaacca    1680
ggccagccac gtttctgcga aaacgcggga aaaagtggaa gcggcgatgg cggagctgaa    1740
ttacattccc aaccgcgtgg cacaacaact ggcgggcaaa cagtcgttgc tgattggcgt    1800
tgccacctcc agtctggccc tgcacgcgcc gtcgcaaatt gtcgcggcga ttaaatctcg    1860
cgccgatcaa ctgggtgcca gcgtggtggt gtcgatggta gaacgaagcg cgtcgaagc    1920 ctgtaaagcg gcggtgcaca atcttctcgc gcaacgcgtc agtgggctga tcattaacta    1980
tccgctggat gaccaggatg ccattgctgt ggaagctgcc tgcactaatg ttccggcgtt    2040
atttcttgat gtctctgacc agacacccat caacagtatt atttttctccc atgaagacgg    2100 tacgcgactg ggcgtggagc atctggtcgc attgggtcac cagcaaatcg cgctgttagc    2160
gggcccatta agttctgtct cggcgcgtct gcgtctggct ggctggcata aatatctcac    2220
tcgcaatcaa attcagccga tagcggaacg ggaaggcgac tggagtgcca tgtccggttt    2280
tcaacaaacc atgcaaatgc tgaatgaggg catcgttccc actgcgatgc tggttgccaa    2340
cgatcagatg gcgctgggcg caatgcgcgc cattaccgag tccgggctgc gcgttggtgc    2400
ggatatctcg gtagtgggat acgacgatac cgaagacagc tcatgttata tcccgccgtt    2460
aaccaccatc aaacaggatt ttcgcctgct ggggcaaacc agcgtggacc gcttgctgca    2520
actctctcag ggccaggcgg tgaagggcaa tcagctgttg cccgtctcac tggtgaaaag    2580
aaaaaccacc ctggcgccca atacgcaaac cgcctctccc cgcgcgttgg ccgattcatt    2640
aatgcagctg gcacgacagg tttcccgact ggaaagcggg cagtgagcgc aacgcaatta    2700
atgtaagtta gcgcgaattg tcgaccaaag cggccatcgt gcctccccac tcctgcagtt    2760
cgggggcatg gatgcgcgga tagccgctgc tggtttcctg gatgccgacg gatttgcact    2820
gccggtagaa ctccgcgagg tcgtccagcc tcaggcagca gctgaaccaa ctcgcgaggg    2880
gatcgagccc ggggtgggcg aagaactcca gcatgagatc cccgcgctgg aggatcatcc    2940
agccggcgtc ccggaaaacg attccgaagc ccaacctttc atagaaggcg gcggtggaat    3000
cgaaatctcg tgatggcagg ttgggcgtcg cttggtcggt catttcgaac cccagagtcc    3060
cgctcagaag aactcgtcaa gaaggcgata gaaggcgatg cgctgcgaat cgggagcggc    3120
gataccgtaa agcacgagga gcggtcagc ccattcgccg ccaagctctt cagcaatatc    3180
acgggtagcc aacgctatgt cctgatagcg gtccgccaca cccagccggc cacagtcgat    3240
gaatccagaa aagcggccat tttccaccat gatattcggc aagcaggcat cgccatgggt    3300
cacgacgaga tcctcgccgt cgggcatgcg cgccttgagc ctggcgaaca gttcggctgg    3360
cgcgagcccc tgatgctctt cgtccagatc atcctgatcg acaagaccgg cttccatccg    3420
agtacgtgct cgctcgatgc gatgtttcgc ttggtggtcg aatgggcagg tagccggatc    3480
aagcgtatgc agccgccgca ttgcatcagc catgatggat actttctcgg caggagcaag    3540
gtgagatgac aggagatcct gccccggcac ttcgcccaat agcagccagt cccttcccgc    3600
ttcagtgaca acgtcgagca cagctgcgca aggaacgccc gtcgtggcca gccacgatag    3660
ccgcgctgcc tcgtcctgca gttcattcag ggcaccggac aggtcggtct tgacaaaaag    3720
aaccgggcgc ccctgcgctg acagccggaa cacggcggca tcagagcagc cgattgtctg    3780
ttgtgcccag tcatagccga atagcctctc cacccaagcg gccggagaac ctgcgtgcaa    3840
tccatcttgt tcaatcatgc gaaacgatcc tcatcctgtc tcttgatcag atcttgatcc    3900
cctgcgccat cagatccttg gcggcaagaa agccatccag tttactttgc agggcttccc    3960
aaccttacca gagggcgccc cagctggcaa ttccggttcg cttgctgtcc ataaaaccgc    4020
```

| | |
|---|---|
| ccagtctagc tatcgccatg taagcccact gcaagctacc tgctttctct ttgcgcttgc | 4080 |
| gttttcccctt gtccagatag cccagtagct gacattcatc cggggtcagc accgtttctg | 4140 |
| cggactggct ttctacgtgt tccgcttcct ttagcagccc ttgcgccctg agtgcttgcg | 4200 |
| gcagcgtg | 4208 |

<210> SEQ ID NO 10
<211> LENGTH: 3984
<212> TYPE: DNA
<213> ORGANISM: Homo sapiens

<400> SEQUENCE: 10

| | |
|---|---|
| aagcttaaaa aactgcaaaa aatagtttga cttgtgagcg gataacaatt aagatgtacc | 60 |
| caattgtgag cggataacaa tttcacacat taaagaggag aaattacata tgaaggatcc | 120 |
| ttggtaccta agtgagtagg gcgtccgatc gacggacgcc ttttttttga attcgtaatc | 180 |
| atggtcatag ctgtttcctg tgtgaaattg ttatccgctc acaattccac acaacatacg | 240 |
| agccggaagc ataaagtgta aagcctgggg tgcctaatga gtgagctaac tcacattaat | 300 |
| tgcgttgcgc tcactgcccg ctttccagtc gggaaacctg tcgtgccagc tgcattaatg | 360 |
| aatcggccaa cgcgcgggga gaggcggttt gcgtattggg cgctcttccg cttcctcgct | 420 |
| cactgactcg ctgcgctcgg tcgttcggct gcggcgagcg gtatcagctc actcaaaggc | 480 |
| ggtaatacgg ttatccacag aatcagggga taacgcagga agaacatgt gagcaaaagg | 540 |
| ccagcaaaag gccaggaacc gtaaaaaggc cgcgttgctg gcgtttttcc ataggctccg | 600 |
| cccccctgac gagcatcaca aaaatcgacg ctcaagtcag aggtggcgaa acccgacagg | 660 |
| actataaaga taccaggcgt ttccccctgg aagctccctc gtgcgctctc ctgttccgac | 720 |
| cctgccgctt accggatacc tgtccgcctt tctcccttcg ggaagcgtgg cgctttctca | 780 |
| tagctcacgc tgtaggtatc tcagttcggt gtaggtcgtt cgctccaagc tgggctgtgt | 840 |
| gcacgaaccc cccgttcagc ccgaccgctg cgccttatcc ggtaactatc gtcttgagtc | 900 |
| caacccggta agacacgact tatcgccact ggcagcagcc actggtaaca ggattagcag | 960 |
| agcgaggtat gtaggcggtg ctacagagtt cttgaagtgg tggcctaact acggctacac | 1020 |
| tagaagaaca gtatttggta tctgcgctct gctgaagcca gttaccttcg gaaaaagagt | 1080 |
| tggtagctct tgatccggca aacaaaccac cgctggtagc ggtggttttt ttgtttgcaa | 1140 |
| gcagcagatt acgcgcagaa aaaaaggatc tcaagaagat cctttgatct tttctacggg | 1200 |
| gtctgacgct cagtggaacg aaaactcacg ttaagggatt ttggtcatga gattatcgtc | 1260 |
| gacaattcgc gcgcgaaggc gaagcggcat gcatttacgt tgacaccatc gaatggtgca | 1320 |
| aaacctttcg cggtatggca tgatagcgcc cggaagagag tcaattcagg gtggtgaatg | 1380 |
| tgaaaccagt aacgttatac gatgtcgcag agtatgccgg tgtctcttat cagaccgttt | 1440 |
| cccgcgtggt gaaccaggcc agccacgttt ctgcgaaaac gcgggaaaaa gtggaagcgg | 1500 |
| cgatggcgga gctgaattac attcccaacc gcgtggcaca caactggcg ggcaaacagt | 1560 |
| cgttgctgat tggcgttgcc acctccagtc tggccctgca cgcgccgtcg caaattgtcg | 1620 |
| cggcgattaa atctcgcgcc gatcaactgg gtgccagcgt ggtggtgtcg atggtagaac | 1680 |
| gaagcggcgt cgaagcctgt aaagcggcgg tgcacaatct tctcgcgcaa cgcgtcagtg | 1740 |
| ggctgatcat taactatccg ctggatgacc aggatgccat tgctgtggaa gctgcctgca | 1800 |
| ctaatgttcc ggcgttattt cttgatgtct ctgaccagac acccatcaac agtattattt | 1860 |

```
tctcccatga agacggtacg cgactgggcg tggagcatct ggtcgcattg ggtcaccagc      1920
aaatcgcgct gttagcgggc ccattaagtt ctgtctcggc gcgtctgcgt ctggctggct      1980
ggcataaata tctcactcgc aatcaaattc agccgatagc ggaacgggaa ggcgactgga      2040
gtgccatgtc cggttttcaa caaccatgca aaatgctgaa tgagggcatc gttcccactg      2100
cgatgctggt tgccaacgat cagatggcgc tgggcgcaat gcgcgccatt accgagtccg      2160
ggctgcgcgt tggtgcggat atctcggtag tgggatacga cgataccgaa gacagctcat      2220
gttatatccc gccgttaacc accatcaaac aggattttcg cctgctgggg caaaccagcg      2280
tggaccgctt gctgcaactc tctcagggcc aggcggtgaa gggcaatcag ctgttgcccg      2340
tctcactggt gaaaagaaaa accaccctgg cgcccaatac gcaaaccgcc tctccccgcg      2400
cgttggccga ttcattaatg cagctggcac gacaggtttc ccgactggaa agcgggcagt      2460
gagcgcaacg caattaatgt aagttagcgc gaattgtcga ccaaagcggc catcgtgcct      2520
ccccactcct gcagttcggg ggcatggatg cgcggatagc cgctgctggt ttcctggatg      2580
ccgacggatt tgcactgccg gtagaactcc gcgaggtcgt ccagcctcag gcagcagctg      2640
aaccaactcg cgagggatc gagcccgggg tgggcgaaga actccagcat gagatccccg       2700
cgctggagga tcatccagcc ggcgtcccgg aaaacgattc cgaagcccaa cctttcatag      2760
aaggcggcgg tggaatcgaa atctcgtgat ggcaggttgg gcgtcgcttg gtcggtcatt      2820
tcgaacccca gagtcccgct cagaagaact cgtcaagaag gcgatagaag gcgatgcgct      2880
gcgaatcggg agcggcgata ccgtaaagca cgaggaagcg gtcagcccat cgccgccaa       2940 gctcttcagc aatatcacgg gtagccaacg ctatgtcctg atagcggtcc gccacaccca      3000
gccggccaca gtcgatgaat ccagaaaagc ggccattttc caccatgata ttcggcaagc      3060
aggcatcgcc atgggtcacg acgagatcct cgccgtcggg catgcgcgcc ttgagcctgg      3120
cgaacagttc ggctggcgcg agcccctgat gctcttcgtc cagatcatcc tgatcgacaa      3180
gaccggcttc catccgagta cgtgctcgct cgatgcgatg tttcgcttgg tggtcgaatg      3240
ggcaggtagc cggatcaagc gtatgcagcc gccgcattgc atcagccatg atggatactt      3300
tctcggcagg agcaaggtga gatgacagga gatcctgccc cggcacttcg cccaatagca      3360
gccagtccct tcccgcttca gtgacaacgt cgagcacagc tgcgcaagga acgcccgtcg      3420
tggccagcca cgatagccgc gctgcctcgt cctgcagttc attcagggca ccggacaggt      3480
cggtcttgac aaaaagaacc gggcgcccct gcgctgacag ccggaacacg gcggcatcag      3540
agcagccgat tgtctgttgt gcccagtcat agccgaatag cctctccacc caagcggccg      3600
gagaacctgc gtgcaatcca tcttgttcaa tcatgcgaaa cgatcctcat cctgtctctt      3660
gatcagatct tgatcccctg cgccatcaga tccttggcgg caagaaagcc atccagttta      3720
ctttgcaggg cttcccaacc ttaccagagg gcgccccagc tggcaattcc ggttcgcttg      3780
ctgtccataa aaccgcccag tctagctatc gccatgtaag cccactgcaa gctacctgct      3840
ttctctttgc gcttgcgttt tcccttgtcc agatagccca gtagctgaca ttcatccggg      3900
gtcagcaccg tttctgcgga ctggctttct acgtgttccg cttcctttag cagcccttgc      3960
gccctgagtg cttgcggcag cgtg                                             3984
```

<210> SEQ ID NO 11
<211> LENGTH: 4277
<212> TYPE: DNA
<213> ORGANISM: Homo sapiens

<400> SEQUENCE: 11

-continued

```
aagcttaaaa aactgcaaaa aatagtttga cttgtgagcg ataacaatt aagatgtacc      60
caattgtgag cggataacaa tttcacacat taaagaggag aaattacata tgtgatagat    120
aaaagacgct gaaaccgaat tcttgttgtc caaactgccg ctggaaaacc cggttctgct    180
ggaccgtttc cacgctacct ccgctgactg ctgcatctcc tacaccacgc gttccatccc    240
gtgctcgctg ctggaatcct acttcgaaac caactccgaa tgctccaaac cgggtgttat    300
cttcctgacc aaaaaaggtc gtcgtttctg cgctaacccg tccgacaaac aggttcaggt    360
ttgtatgcgt atgctgaaac tggacacccg tgcggccgct ctagaggatc ctcgaggtac    420
ctaagtgagt agggcgtccg atcgacggac gccttttttt tgaattcgta atcatggtca    480
tagctgtttc ctgtgtgaaa ttgttatccg ctcacaattc cacacaacat acgagccgga    540
agcataaagt gtaaagcctg gggtgcctaa tgagtgagct aactcacatt aattgcgttg    600
cgctcactgc ccgctttcca gtcgggaaac ctgtcgtgcc agctgcatta atgaatcggc    660
caacgcgcgg ggagaggcgg tttgcgtatt gggcgctctt ccgcttcctc gctcactgac    720
tcgctgcgct cggtcgttcg gctgcggcga gcggtatcag ctcactcaaa ggcggtaata    780
cggttatcca cagaatcagg ggataacgca ggaaagaaca tgtgagcaaa aggccagcaa    840
aaggccagga accgtaaaaa ggccgcgttg ctggcgtttt tccataggct ccgcccccct    900
gacgagcatc acaaaaatcg acgctcaagt cagaggtggc gaaacccgac aggactataa    960
agataccagg cgtttccccc tggaagctcc ctcgtgcgct ctcctgttcc gaccctgccg   1020
cttaccggat acctgtccgc ctttctccct tcgggaagcg tggcgctttc tcatagctca   1080
cgctgtaggt atctcagttc ggtgtaggtc gttcgctcca agctgggctg tgtgcacgaa   1140
ccccccgttc agcccgaccg ctgcgcctta tccggtaact atcgtcttga gtccaacccg   1200
gtaagacacg acttatcgcc actggcagca gccactggta acaggattag cagagcgagg   1260
tatgtaggcg gtgctacaga gttcttgaag tggtggccta actacggcta cactagaaga   1320
acagtatttg gtatctgcgc tctgctgaag ccagttacct tcggaaaaag agttggtagc   1380
tcttgatccg gcaaacaaac caccgctggt agcggtggtt ttttttgtttg caagcagcag   1440
attacgcgca gaaaaaaagg atctcaagaa gatcctttga tcttttctac ggggtctgac   1500
gctcagtgga acgaaaactc acgttaaggg attttggtca tgagattatc gtcgacaatt   1560
cgcgcgcgaa ggcgaagcgg catgcattta cgttgacacc atcgaatggt gcaaaacctt   1620
tcgcggtatg gcatgatagc gcccggaaga gagtcaattc agggtggtga atgtgaaacc   1680
agtaacgtta tacgatgtcg cagagtatgc cggtgtctct tatcagaccg tttcccgcgt   1740
ggtgaaccag gccagccacg tttctgcgaa aacgcgggaa aaagtggaag cggcgatggc   1800
ggagctgaat tacattccca accgcgtggc acaacaactg gcgggcaaac agtcgttgct   1860
gattggcgtt gccacctcca gtctggccct gcacgcgccg tcgcaaattg tcgcggcgat   1920
taaatctcgc gccgatcaac tgggtgccag cgtggtggtg tcgatggtag aacgaagcgg   1980
cgtcgaagcc tgtaaagcgg cggtgcacaa tcttctcgcg caacgcgtca gtgggctgat   2040
cattaactat ccgctggatg accaggatgc cattgctgtg gaagctgcct gcactaatgt   2100
tccggcgtta tttcttgatg tctctgacca gacacccatc aacagtatta ttttctccca   2160
tgaagacggt acgcgactgg gcgtggagca tctggtcgca ttgggtcacc agcaaatcgc   2220
gctgttagcg ggcccattaa gttctgtctc ggcgcgtctg cgtctggctg ctggcataa   2280
atatctcact cgcaatcaaa ttcagccgat agcggaacgg gaaggcgact ggagtgccat   2340
```

```
gtccggtttt caacaaacca tgcaaatgct gaatgagggc atcgttccca ctgcgatgct    2400
ggttgccaac gatcagatgg cgctgggcgc aatgcgcgcc attaccgagt ccgggctgcg    2460
cgttggtgcg gatatctcgg tagtgggata cgacgatacc gaagacagct catgttatat    2520
cccgccgtta accaccatca acaggatttt cgcctgctg gggcaaacca gcgtggaccg     2580
cttgctgcaa ctctctcagg gccaggcggt gaagggcaat cagctgttgc ccgtctcact    2640
ggtgaaaaga aaaccaccc tggcgcccaa tacgcaaacc gcctctcccc gcgcgttggc     2700
cgattcatta atgcagctgg cacgacaggt tcccgactg gaaagcgggc agtgagcgca     2760
acgcaattaa tgtaagttag cgcgaattgt cgaccaaagc ggccatcgtg cctccccact    2820
cctgcagttc gggggcatgg atgcgcggat agccgctgct ggtttcctgg atgccgacgg    2880
atttgcactg ccggtagaac tccgcgaggt cgtccagcct caggcagcag ctgaaccaac    2940
tcgcgagggg atcgagcccg ggtgggcga agaactccag catgagatcc ccgcgctgga     3000
ggatcatcca gccggcgtcc cggaaaacga ttccgaagcc caacctttca tagaaggcgg    3060
cggtggaatc gaaatctcgt gatgcaggt tgggcgtcgc ttggtcggtc atttcgaacc     3120
ccagagtccc gctcagaaga actcgtcaag aaggcgatag aaggcgatgc gctgcgaatc    3180
gggagcggcg ataccgtaaa gcacgaggaa gcggtcagcc cattcgccgc caagctcttc    3240
agcaatatca cgggtagcca acgctatgtc ctgatagcgg tccgccacac ccagccggcc    3300
acagtcgatg aatccagaaa agcggccatt ttccaccatg atattcggca agcaggcatc    3360
gccatgggtc acgacgagat cctcgccgtc gggcatgcgc gccttgagcc tggcgaacag    3420
ttcggctggc gcgagcccct gatgctcttc gtccagatca tcctgatcga caagaccggc    3480
ttccatccga gtacgtgctc gctcgatgcg atgtttcgct tggtggtcga atgggcaggt    3540
agccggatca agcgtatgca gccgccgcat tgcatcagcc atgatggata ctttctcggc    3600
aggagcaagg tgagatgaca ggagatcctg ccccggcact cgcccaata gcagccagtc     3660 ccttcccgct tcagtgacaa cgtcgagcac agctgcgcaa ggaacgcccg tcgtggccag    3720
ccacgatagc cgcgctgcct cgtcctgcag ttcattcagg gcaccggaca ggtcggtctt    3780
gacaaaaaga accgggcgcc cctgcgctga cagccggaac acggcggcat cagagcagcc    3840
gattgtctgt tgtgcccagt catagccgaa tagcctctcc acccaagcgg ccggagaacc    3900
tgcgtgcaat ccatcttgtt caatcatgcg aaacgatcct catcctgtct cttgatcaga    3960
tcttgatccc ctgcgccatc agatccttgg cggcaagaaa gccatccagt ttactttgca    4020
gggcttccca accttaccag agggcgcccc agctggcaat tccggttcgc ttgctgtcca    4080
taaaaccgcc cagtctagct atcgccatgt aagcccactg caagctacct gctttctctt    4140
tgcgcttgcg ttttcccttg tccagatagc ccagtagctg acattcatcc ggggtcagca    4200
ccgtttctgc ggactggctt tctacgtgtt ccgcttcctt tagcagccct gcgccctga     4260 gtgcttgcgg cagcgtg                                                   4277
```

<210> SEQ ID NO 12
<211> LENGTH: 77
<212> TYPE: PRT
<213> ORGANISM: Homo sapiens

<400> SEQUENCE: 12

```
Met Asp Arg Phe His Ala Thr Ser Ala Asp Cys Cys Ile Ser Tyr Thr
 1               5                  10                  15

Pro Arg Ser Ile Pro Cys Ser Leu Leu Glu Ser Tyr Phe Glu Thr Asn
            20                  25                  30
```

Ser Glu Cys Ser Lys Pro Gly Val Ile Phe Leu Thr Lys Lys Gly Arg
            35                  40                  45

Arg Phe Cys Ala Asn Pro Ser Asp Lys Gln Val Gln Val Cys Met Arg
            50                  55                  60

Met Leu Lys Leu Asp Thr Arg Ile Lys Thr Arg Lys Asn
 65                  70                  75

<210> SEQ ID NO 13
<211> LENGTH: 319
<212> TYPE: PRT
<213> ORGANISM: Homo sapiens

<400> SEQUENCE: 13

Met Ala Glu Leu Asn Tyr Ile Pro Asn Arg Val Ala Gln Gln Leu Ala
  1               5                  10                  15

Gly Lys Gln Ser Leu Leu Ile Gly Val Ala Thr Ser Ser Leu Ala Leu
             20                  25                  30

His Ala Pro Ser Gln Ile Val Ala Ile Lys Ser Arg Ala Asp Gln
             35                  40                  45

Leu Gly Ala Ser Val Val Ser Met Val Glu Arg Ser Gly Val Glu
             50                  55                  60

Ala Cys Lys Ala Ala Val His Asn Leu Leu Ala Gln Arg Val Ser Gly
 65                  70                  75                  80

Leu Ile Ile Asn Tyr Pro Leu Asp Asp Gln Asp Ala Ile Ala Val Glu
                 85                  90                  95

Ala Ala Cys Thr Asn Val Pro Ala Leu Phe Leu Asp Val Ser Asp Gln
            100                 105                 110

Thr Pro Ile Asn Ser Ile Ile Phe Ser His Glu Asp Gly Thr Arg Leu
            115                 120                 125

Gly Val Glu His Leu Val Ala Leu Gly His Gln Gln Ile Ala Leu Leu
            130                 135                 140

Ala Gly Pro Leu Ser Ser Val Ser Ala Arg Leu Arg Leu Ala Gly Trp
145                 150                 155                 160

His Lys Tyr Leu Thr Arg Asn Gln Ile Gln Pro Ile Ala Glu Arg Glu
                165                 170                 175

Gly Asp Trp Ser Ala Met Ser Gly Phe Gln Gln Thr Met Gln Met Leu
            180                 185                 190

Asn Glu Gly Ile Val Pro Thr Ala Met Leu Val Ala Asn Asp Gln Met
            195                 200                 205

Ala Leu Gly Ala Met Arg Ala Ile Thr Glu Ser Gly Leu Arg Val Gly
            210                 215                 220

Ala Asp Ile Ser Val Val Gly Tyr Asp Asp Thr Glu Asp Ser Ser Cys
225                 230                 235                 240

Tyr Ile Pro Pro Leu Thr Thr Ile Lys Gln Asp Phe Arg Leu Leu Gly
                245                 250                 255

Gln Thr Ser Val Asp Arg Leu Leu Gln Leu Ser Gln Gly Gln Ala Val
            260                 265                 270

Lys Gly Asn Gln Leu Leu Pro Val Ser Leu Val Lys Arg Lys Thr Thr
            275                 280                 285

Leu Ala Pro Asn Thr Gln Thr Ala Ser Pro Arg Ala Leu Ala Asp Ser
            290                 295                 300

Leu Met Gln Leu Ala Arg Gln Val Ser Arg Leu Glu Ser Gly Gln
305                 310                 315

-continued

```
<210> SEQ ID NO 14
<211> LENGTH: 264
<212> TYPE: PRT
<213> ORGANISM: Homo sapiens

<400> SEQUENCE: 14

Met Ile Glu Gln Asp Gly Leu His Ala Gly Ser Pro Ala Ala Trp Val
 1               5                  10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
        50                  55                  60

Ala Arg Leu Ser Trp Leu Ala Thr Thr Gly Val Pro Cys Ala Ala Val
 65                 70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
               100                 105                 110

Val Ser Ile Met Ala Asp Ala Met Arg Arg Leu His Thr Leu Asp Pro
           115                 120                 125

Ala Thr Cys Pro Phe Asp His Gln Ala Lys His Arg Ile Glu Arg Ala
       130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
               165                 170                 175

Arg Met Pro Asp Gly Glu Asp Leu Val Val Thr His Gly Asp Ala Cys
           180                 185                 190

Leu Pro Asn Ile Met Val Glu Asn Gly Arg Phe Ser Gly Phe Ile Asp
       195                 200                 205

Cys Gly Arg Leu Gly Val Ala Asp Arg Tyr Gln Asp Ile Ala Leu Ala
   210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
               245                 250                 255

Tyr Arg Leu Leu Asp Glu Phe Phe
           260
```

EXPRESSION CONTROL SEQUENCES

This is a continuation in part of U.S. application Ser. No. 08/941,020 filed Sep. 30, 1997, now abandoned.

FIELD OF THE INVENTION

The present invention relates to highly efficient and highly repressible expression control sequences, expression vectors which contain these expression control sequences, microorganisms transformed with these expression vectors, and methods for their production by means of recombinant DNA technology. The present invention also relates to methods for the production of viral, prokaryotic, and eukaryotic proteins and fragments thereof using these highly repressible expression control sequences, expression vectors and transformed microorganisms.

BACKGROUND OF THE INVENTION

The level of production of a protein in a host cell is determined by three major factors: the number of copies of its structural gene within the cell, the efficiency with which the structural gene copies are transcribed and the efficiency with which the resulting messenger RNA ("mRNA") is translated. The transcription and translation efficiencies are, in turn, dependent on nucleotide sequences which are normally situated ahead of the desired structural genes or the translated sequence. These nucleotide sequences (expression control sequences) define, inter alia, the location at which the RNA polymerase binds (the promoter sequence to initiate transcription; see also EMBO J. 5:2995–3000 (1986)) and at which the ribosomes bind and interact with the mRNA (the product of transcription) to initiate translation.

Not all expression control sequences have the same efficiency. It is therefore often advantageous to separate the specific coding sequence for a desired protein from its adjacent nucleotide sequences and to link it with other expression control sequences to achieve a higher expression rate. After this linkage has been accomplished, the newly combined DNA fragment can be inserted into a plasmid capable of achieving a high copy number or a derivative of a bacteriophage to increase the structural gene copies within the cell, thereby improving the yield of the desired protein.

The constitutive expression of overproduction of both toxic and normally nontoxic gene products is often harmful to the host cells, thereby, lowering the stability of a specific host cell-vector system. Therefore, an expression control sequence should, in addition to improving the transcription and translation efficiency of a cloned gene, be regulatable to permit the regulation of the expression during the growth of the microorganisms. Some regulatable expression control sequences can be switched off during the growth of the host cells and then can be switched on again at a desired point in time, to favor the expression of large amounts of the desired protein.

Various expression control sequences have been used to regulate the expression of DNA sequences and genes which code for desired proteins. See, e.g., Itakura et al.(1977) Science 198:1056–1063; Goeddel et al. (1979) Proc. Natl. Acad. Sci. U.S.A. 76:106–110; Emtage et al. (1980) Nature 283:171–174; Bernard et al. (1979) Sciences 205:602–607; Ammann et al. (1983) Gene 25:167–178; de Boer et al. (1983) Proc. Natl. Acad. Sci. U.S.A. 80:21–25; European Patent Application Publication Nos. 41767 and 186069.

SUMMARY OF THE INVENTION

In accordance with the invention, highly efficient and highly repressible expression control sequences can be produced by combining promoter sequences with operator/repressor sequences. The present invention provides for expression control sequences for the expression of polypeptides from a gene or polynucleotide of interest. The gene or polynucleotide may express a viral, prokaryotic, or eukaryotic polypeptide. These control sequences are produced by combining bacterial or phage promoter and operator/repressor systems.

More particuarly, the present invention provides for DNA expression control sequences comprising at least a portion of one or more lac operator sequences and a phage promoter comprising a −30 region, having a sequence represented by the sequence 5' TTGMYW 3' (where M=A or C and Y=C or T and W=A or T), and a −12 region, having a sequence represented by the sequence 5' TAWRMT (where R=A or G).

The present invention further provides for DNA expression control sequences comprising at least a portion of one or more lac operator sequences and a phage promoter comprising a −30 region, having a sequence represented by the sequence 5' TTGAYA 3' (where Y=C or T), and a −12 region, having a sequence represented by a sequence selected from the group consisting of: 5' TAWRTT 3' (where R=A or G), 5' TAWGMT 3' (where W=A or T and M=A or C), and 5' TAARMT 3'.

The present invention further provides for DNA expression control sequences comprising at least a portion of one or more lac operator sequences and a phage promoter comprising a −30 region, having a sequence represented by the sequence 5' TTGMTW 3' (where M=A or C and W=A or T), and a −12 region, having a sequence represented by a sequence selected from the group consisting of: 5' TAWRTT 3' (where R=A or G), 5' TAWGMT 3', and 5' TAARMT 3'.

The present invention further provides for DNA expression control sequences comprising at least a portion of one or more lac operator sequences and a phage promoter comprising a −30 region, having a sequence represented by the sequence 5' TTGCTW 3' (where Y=C or T and W=A or T), and a −12 region, having a sequence represented by a consensus sequence selected from the group consisting of: 5' TAWRTT 3' (where R=A or G), 5' TAWGMT 3' (where M=A or C), and 5' TAARMT 3'.

The present invention further provides for DNA expression control sequences comprising at least a portion of one or more lac operator sequences and a phage promoter comprising a −30 region, having the sequence 5' TTGACT 3', and a −12 region, having the sequence 5' TAAGAT 3'.

The present invention further provides for expression vectors comprising the above expression control sequences, host cells transformed with such expression vectors, and methods for producing viral, prokaryotic, and eukaryotic polypeptides using the disclosed expression control sequences.

BRIEF DESCRIPTION OF THE FIGURES

FIG. 1 shows the nucleotide sequence of expression control sequences of the present invention designated: M (SEQ ID NO:4), M+D (SEQ ID NO:5), U+D (SEQ ID NO:6), M+D1 (SEQ ID NO:7), and M+D2 (SEQ ID NO:8). The start of transcription is represented by the bolded letter A labelled with an arrow and is designated as +1. The promoter regions −35 to −30 and −12 to −7 are bolded. Operator sequences are underlined. Underlined bases of the promoter regions share the same sequence as the operator and are, therefore, designated as both operator and promoter sequences.

FIGS. 2A–2G show the nucleotide sequence of an expression vector comprising expression control sequence M+D1 (SEQ ID NO:07) and the MPIF-1Δ23 gene (SEQ ID NO:12) and illustrates relevant features of the expression vector (SEQ ID NOS:9, 13 and 14).

DETAILED DESCRIPTION OF THE INVENTION

Promoter sequences which can be used in this invention include natural promoter sequences and functional variants, which have been specifically altered by mutation or synthesis, and combinations of these promoter sequences. The promoter sequences can routiney be obtained from: gram-negative organisms, including but not limited to, gram negative bacteria, such as *E. coli*; from gram-positive organisms, such as *B. subtilis* and *B. stearothermophilis;* and from the corresponding phages that infect these organisms. Preferred promoter sequences are those from T-coliphages. Espeicaly preferred, are T5 phage promoter sequences.

Operator/repressor systems that can be used according to the present invention include all systems that are directly inducible by chemical inducers which produce, in the natural state or after corresponding variations (e.g., by mutation), repression factors. In preferred embodiments, the directly inducible systems of the present invention are not inducible by SOS function (lexA/recA system) or by temperature, such as the $P_L$ operator/repressor system.

Examples of systems which are directly regulatable by chemical induction include, but are not limited to, the regulation units of the lactose, galactose, tryptophan and tetracycline operons, and other negatively controllable operons (i.e., operons which are regulatable by an operator/repressor action. See, e.g., Miller et al., *The operon* (Cold Spring Harbor Laboratory 1980); Hillen et al., (1984) J. Mol. Biol. 172:185–201. Especially preferred operator/repressor systems are the natural lac-operator/repressor system, see, e.g., Miller et al., *The operon* (Cold Spring Harbor Laboratory 1980), and variants of the above-named operator/-repressor systems, which are specifically modified by mutation.

LacIq is an allele of the lacI gene which confers tight regulation of the lac operator. See E. Amann et al., (1988) Gene 69:301–305; M. Stark Gene (1987) 51:255–267. The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). An expression vector comprising a gene of interest under the control of the expression control sequences which comprise the lac operator will not produce appreciable quantities of protein in uninduced host cells. Induction of host cells by the addition of an agent such as IPTG, however, results in the expression of the protein encoded by the gene of interest.

The phage promoter sequences can be used with one or more operator/repressor system(s) to produce the desired expression control sequences. When a single operator/repressor system is used, a full or partial operator sequence can be located either within or outside the promoter sequence, can partially replace the promoter, or can be located before or after the promoter sequence. In preferred emobodiments, a full or partial operator/repressor system is integrated into the promoter sequence. In an especially preferred emobodiment, the integration position of the operator sequence is the spacer region between position –12 and –30 (nomenclature as in FIG. 1), wherein +1 is designated as the start of transcription and –1 is designated as the adjacent base 5' to the start of transcription.

When two or more operator/repressor systems are used, both operators can be located within or outside the promoter sequence, or alternatively one operator can be situated within and another outside the promoter sequence. The operator sequence located outside the promoter spacer may be either 5' or 3' of the promoter region. That is, the operator may be either upstream of the –30 promoter region or downstream of the –12 promoter region. Preferably, one operator/repressor is integrated into the spacer region (between the –12 and –30 promoter regions) and a second operator/repressor is integrated either upstream or downstream (5' or 3') of the promoter regions (–30 and –12). More preferably, one operator/repressor is integrated into the spacer region and the other is integrated downstream (3') of the –12 promoter region, so that repressor binding will create maximal cooperatively between the two operator sequences of the operator/repressor systems.

The invention further provides for a ribosome binding site (Shine-Dalgarno (S/D) sequence) downstream of the start of transcription and upstream from the start of translation, (usually about 10 nucleotide bases). Preferred ribosome binding site sequences comprise the sequence 5'-GAGGAC-3'. A more preferred ribosome binding site sequence comprises the sequence 5'-ATTAAAGAGGAGAAATTA-3' (SEQ ID NO:1).

The invention additionally provides for one or more restriction enzyme sites downstream of the ribosome binding site sequence for cloning and expressing a gene or polynucleotide of interest. A preferred restriction enzyme site is NdeI which recognizes and cleaves the sequence 5'-CATATG-3'. A preferred location for the NdeI site is at the 5'-ATG-3' initiation codon downstream of the ribosome binding site sequence which will permit proper positioning of the gene of interest for translation at the correct codon and in the correct frame.

As discussed above, the T5 promoter sequences of the present invention comprise two critical elements located between positions –30 to –35, called the –30 region, and –7 to –12, called the –12 region. In a preferred embodiment the –30 region comprises any sequence represented by the sequence 5' TTGMYW 3' (where M=A or C, Y=C or T, and W=A or T). More preferred are any –30 sequences represented by sequences 5' TTGATA 3', 5' TTGMTW 3', or 5' TTGCTW 3'. Even more preferably the –30 region comprises the sequence 5' TTGACA 3'.

In a preferred embodiment the –12 region comprises any sequence represented by the sequence 5' TAWRMT 3' (where R=A or G). In a more preferred embodiment, the –12 region promoter is represented by the sequences, 5' TATAMT 3', 5' TAWAMT 3', 5' TAARAT 3', or 5' TAWAMT 3'. In a most preferred embodiment, the –12 region promoter comprises the sequence 5' TAAGAT 3' and the –35 region comprises the sequence 5' TTGACT 3'. The invention also provides for the exclusion of any –30 promoter region represented by the sequence 5' TTGMYW 3' and any –12 promoter region represented by the sequence 5' TAWRMT 3'.

The lac operator sequences of the present invention comprises the entire lac operator sequence represented by the sequence 5' AATTGTGAGCGGATAACAATTTCA-CACA 3' (SEQ ID. NO:2) or a portion thereof that retains at least partial activity. Activity is routinely determined using techniques well known in the art to measure the relative repressability of a promoter sequence in the absence of an inducer such as IPTG. This is done by comparing the relative amounts of protein expressed from expression control sequences comprising portions of the lac operator sequence and full length lac operator sequence. The partial operator sequence is measured relative to the full length lac operator sequence (SEQ ID NO:2). In one embodiment, partial activity for the purposes of the present invention means activity not less then 100 fold reduced relative to the full length sequence. In alternative embodiments, partial activity for the purpose of the present invention means activity not less than 75, 50, 25, 20, 15, and 10 fold reduced relative to the full length lac operator sequence. In a preferred embodiment, the ability of a partial sequence to repress is not less than 10 fold reduced relative to the full length sequence.

In a preferred embodiment the expression control sequences comprise a T5 phage promoter sequence and two lac operator sequences wherein at least a portion of the full length lac operator sequence (SEQ ID NO:2) is located within the spacer region between −12 and −30 of the expression control sequences. A preferred portion of an operator sequence comprises at least the sequence 5'-GTGAGCGGATAACAAT-3' (SEQ ID NO:3). The precise location of operator sequences are designated using the nomenclature as in FIG. 1, wherein the 5' base position of the sequence 5'-GTGAGCGGATAACAAT-3' (SEQ ID NO:3) is described. In another preferred embodiment, the operator sequences comprise the sequence 5'-GTGAGCGGATAACAAT-3' (SEQ ID NO:3); wherein the 5' G occupies any base position between −75 and +50. An example of this preferred embodiment is the expression control sequence M+D 1 wherein the operator sequences comprise the sequence 5'-GTGAGCGGATAACAAT-3' (SEQ ID NO:3) and are located at positions −28 and +5.

The expression control sequences of the present invention can be produced by recombinant DNA techniques, or alternatively, can be synthesized in whole or in part, using chemical methods known in the art. See, e.g., Caruthers et al. (1980) Nuc. Acids. Res. 7:215–233; Crea and Hom, (1980) Nuc. Acids. Res. 9(10):2331; Matteucci and Caruthers, (1980) Tetrahedron Letters 21:719. Expression control sequences of the present invention have been obtained by chemical DNA synthesis, whereby functional parts of the lac-operator sequence have been combined with functional parts of a T5 promoter sequence. Preferred are expression control sequences, M (SEQ ID NO:4), M+D (SEQ ID NO:5), U+D (SEQ ID NO:6), M+D1 (SEQ ID NO:7), and M+D2 (SEQ ID NO:8), (See FIG. 1.).

The previously mentioned lac-operator sequences are negatively regulated by the lac-repressor. The corresponding repressor gene can be introduced into the host cell in a vector or through integration into the chromosome of a bacterium by known methods, such as by integration of the lacIq gene. See, e.g., Miller et al, supra; Calos, (1978) Nature 274:762–765. The vector encoding the repressor molecule may be the same vector that contains the expression control sequences and a gene or polynucleotide of interest or may be a separate and distinct vector. Preferably, the repressor gene is encoded on the vector containing the expression control sequences and a gene or polynucleotide of interest. An advantage of having the repressor gene encoded on same vector that contains the expression control sequences and gene of interest is that the ratio of repressor protein to plasmid copy number may be more consistent than the other alternatives above. This may allow better regulation of repression and also provide for greater predictability of the extent of repression. Another advantage is that it is not necessary to maintain multiple vectors in a single host cell or to integrate the repressor gene into the bacterial chromosome.

The expression control sequences of the invention can routinely be inserted using procedures known in the art into any suitable expression vector which can replicate in gram-negative and/or gram-positive bacteria. See, e.g., Sambrook et al. *Molecular Cloning: A Laboratory Manual* (Cold Spring Harbor, N.Y. 2nd ed. 1989); Ausubel et al., *Current Protocals in Molecular Biology* (Green Pub. Assoc. and Wiley Intersciences, N.Y.). Suitable vectors can be constructed from segments-of chromosomal, nonchromosomal and synthetic DNA sequences, such as various known plasmid and phage DNA's. See, e.g., Sambrook et al. Molecular Cloning: A Laboratory Manual (Cold Spring Harbor, N.Y. 2nd ed. 1989). Especially suitable vectors are plasmids of the pDS family. See Bujard et al, (1987) Methods in Enzymology, 155:416–4333. Examples of preferred suitable plasmids are pBR322 and pBluescript (Stratagene, La Jolla, Calif.) based plamids. More preferred examples of suitable plasmids are pUC based vectors including pUC18 and pUC19 (New England Biolabs, Beverly, Mass.) and pREP4 (Qiagen Inc., Chatsworth, Calif.). Portions of vectors encoding desired functions may also be combined to form new vectors with desired characteristics. For example, the origin of replication of pUC19 may be recombined with the kanamycin resistance gene of pREP4 to create a new vector with both desired characteristics.

Preferably, vectors comprising the expression control sequences also contain sequences that allow replication of the plasmid to high copy number in the host bacteria of choice. Additionally, vectors comprising the expression control sequences may further comprise a multiple cloning site immediately downstream of the expression control sequences and ribosomal binding site.

Vectors comprising the expression control sequences may further comprise genes conferring antibodic resistance. Preferred genes are those conferring resistence to ampicillian, chloramphenicol, and tetracyclin. Especially preferred genes are those conferring resistance to kanamycin.

The expression control sequences of the invention can also be inserted into the chromosome of gram-negative and gram-positive bacterial cells using techniques known in the art. In this case, selection agents such as antibiotics, which are generally required when working with vectors, can be dispensed with.

In another embodiment, vectors containing the expression control sequences of the invention additionally contain polynucleotide sequences expressed under the control of the expression control sequences. In a specific embodiment, host cells are transformed with vectors containing the expression control sequences of the invention and multiple copies of the vectors are harvested from the transformants.

Polynucleotide sequences which can be expressed using the expression control sequences of the invention include those which code in vivo or in vitro for viral, prokaryotic, or eukaryotic proteins. For example, such DNA sequences can code for: enzymes; hormones; proteins having immunoregulatory, antiviral or antitumor activity; antibodies and fragments thereof (e.g., Fab, F(ab), F(ab)$_2$, single-chain Fv, disulfide-linked Fv); antigens; and other useful viral, prokaryotic, or eukaryotic proteins.

In one embodiment of the invention, a desired protein is produced by a method comprising:
(a) transforming a bacterium such as *E. coli, S. typhimurium* or *B. subtilis,* with an expression vector in which DNA which codes for a desired viral, prokaryotic, or eukaryotic protein is operably linked to an aforementioned expression control sequence;

(b) culturing the transformed bacterium under suitable growth conditions; and (c) isolating the desired protein from the culture.

In another embodiment of the invention, a desired protein is produced by a method comprising:

(a) inserting an aforementioned expression control sequence, which is operably linked to the coding sequence of a desired viral, prokaryotic, or eukaryotic protein, into the chromosome of a suitable bacterium;

(b) cultivating of the thus-obtained bacterium under suitable growth conditions; and (c) isolating the desired protein from the culture.

The selection of a suitable host organism is determined by various factors which are well known in the art. Factors to be considered include, for example, compatibility with the selected vector, toxicity of the expression product, expression characteristics, necessary biological safety precautions and costs.

Suitable host organisms include, but are not limited to, gram-negative and gram-positive bacteria, such as E. coli, S. typhimurium, and B. subtilis strains. Preferred E. coli strains include DH5α (Gibco-BRL, Gaithersberg, Md.), XL-1 Blue (Stratagene), and W3110 (ATCC No. 27325). Other E. coli strains that can be used according to the present invention include other generally available strains such as E. coli 294 (ATCC No. 31446), E. coli RR1 (ATCC No. 31343) and M15.

EXAMPLES

The examples which follow are set forth to aid in understanding the invention but are not intended to, and should not be construed to, limit its scope in any way. The examples do not include detailed descriptions for conventional methods employed in the construction of vectors, the insertion of genes encoding polypeptides of interest into such vectors or the introduction of the resulting plasmids into bacterial hosts. Such methods are described in numerous publications and can be carried out using recombinant DNA technology methods which are well known in the art See, e.g., Sambrook et al. *Molecular Cloning: A Laboratory Manual* (Cold Spring Harbor, N.Y. 2nd ed. 1989); Ausubel et al., *Current Protocols in Molecular Biology* (Green Pub. Assoc. and Wiley Intersciences, N.Y.).

Expression control sequences M (SEQ ID NO:4), M+D (SEQ ID NO:5), U+D (SEQ ID NO:6), M+D1 (SEQ ID NO:7), and M+D2 (SEQ ID NO:8), represented in FIG. 1, comprising a T5 and lac operator sequences were designed de novo and then chemically synthesized. Restricion enzyme sites (e.g. HindIII and NdeI) were designed at the 5' and 3' ends of the oligonucleotides to facilitate cloning. The sequences were synthesized as single stranded fragments and hybridized as complementary fragments to produce overlapping double stranded fragments. The overlapping fragments were then extended using DNA polymerase, cleaved with restriction enzymes, and cloned into a plasmid vector. The plasmid vector was constructed by ligating a 2.7 Kb HindIII to SalI fragment comprising the kanamycin resistance gene and the lac repressor from pREP4 (Qiagen Inc., Chatsworth, Calif.) with the origin of replication from the pUC19 vector (LTI, Gaithersburg, Md.). Expression vectors were assembled by individually ligating the chemically synthesized expression control sequences with the vector comprising the kanamycin resistance gene, lac repressor, and pUC19 origin of replication.

To determine the relative promoter strengths and level of repressibility between the expression control sequences, a gene was ligated in an NdeI site approximately 10 bases 3' of the ribosome binding site. The gene used was the MPIF-1Δ23 gene which codes for a novel human β-chemokine. The mature form of MPIF-1Δ23 is a 76 amino acid peptide (SEQ ID NO:12). The expression vector pHE4-5 comprising the expression control sequence M+D1 (SEQ ID NO:7) and the MPIF-1Δ23 gene is represented in FIGS. 2A–2G (SEQ ID NO:9).

To express protein from the expression vectors E. coli cells were transformed with the expression vectors and grown in overnight (O/N) cultures supplemented with kanamycin (25 ug/ml) to an opitical density 600λ (O.D. 600) of between 0.4 and 0.6. IPTG was then added to a final concentration of 1 mM. IPTG induced cultures were grown for an additional 3–4 hours. Cells were then harvested using methods known in the art and the level of protein was detected using Western blot analysis. The results varied with the expression control sequence M+D1 (SEQ ID NO:7) demonstrating unexpectedly high levels of repression, in the absence of IPTG, and high levels of induced expression in the presence of IPTG.

Two other plasmids, pHE4-0 (SEQ ID NO:10) and pHE4a (SEQ ID NO:11) were constructed to facilitate cloning of other genes or polynucleotides of interest. pHE4-0 was constructed using an expression vector comprising the expression control sequence M+D1 (SEQ ID NO:17) and the MPEF-1Δ23 gene. pHE4-0 was constructed by removing the sequence between the NdeI and Asp718 sites, comprising the MPIF-1Δ23 gene, and replacing it with a polylinker comprising a BamHI site. pHE4a was constructed in a similar manner, but the sequence between the NdeI and Asp718 sites, comprising the MPIF-1Δ23 gene, was replaced by a polylinker comprising XbaI, BamHI, and XhoI restriction sites and an additional "stuffer" fragment of approximately 300 bp in length. The stuffer fragment is used to indictate whether the polylinker (multiple cloning site) has been efficiently digested when two restriction enzymes are used in cloning a gene or polynucleotide of interest. For example, after digesting the DNA with the appropriate restriction enzymes, e.g. NdeI and Asp718, a portion of the digested vector is assayed by agarose gel electrophoresis. The presence of an approximately 300 bp fragment indicates the vector was properly cleaved with both enzymes.

Deposit of Microorganisms

Plasmid pHE4a has been deposited with the American Type Culture Collection, 10801 University Boulevard, Manassas, Va. 20110-2209 on Feb. 25, 1998 under accession number 209645. These cultures have been accepted for deposit under the provisions the Budapest Treaty on the International Recognition of Microorganisms for the Purposes of Patent Proceedings. Applicants have directed that the plasmids be made available without restriction to the general public upon the issuance of a United States patent.

The disclosure of all publications (including patents, patent applications, journal articles, laboratory manuals, books, or other documents) cited herein are hereby incorporated by reference in their entireties.

The present invention is not to be limited in scope by the specific embodiments described herein, which are intended as single illustrations of individual aspects of the invention. Functionally equivalent methods and components are within the scope of the invention, in addition to those shown and described herein and will become apparant to those skilled in the art from the foregoing description and accompanying drawings. Such modifications are intended to fall within the scope of the appended claims.

We claim:

1. An isolated DNA expression control sequence comprising: at least one lac operator sequence comprising the sequence 5' GTGAGCGGATAACAAT 3' (SEQ ID NO:3); a −30 region having a sequence represented by the sequence 5' TTGACT 3'; and a −12 region having a sequence represented by the sequence 5' TAWRMT (where W=A or T and R=A or G and M=A or C); with the proviso that the −12 region is not 5' KATAMT 3' (where K=G or T).

2. An isolated DNA expression control sequence comprising: at least one lac operator sequence comprising the sequence 5' GTGAGCGGATAACAAT 3' (SEQ ID NO:3); a −30 region having a sequence represented by the sequence 5' TTGAYA 3' (where Y=C or T); and a −12 region having a sequence represented by a sequence selected from the group consisting of: 5' TAARTT 3' (where R=A or G), 5' TATGMT 3' (where M=A or C), and 5' TAAGCT 3'.

3. An isolated DNA expression control sequence comprising: at least one lac operator sequence comprising the sequence 5' GTGAGCGGATAACAAT 3' (SEQ ID NO:3); a −30 region having a sequence represented by the sequence 5' TTGMTW 3' (where M=A or C and W=A or T); and a −12 region having a sequence represented by a sequence selected from the group consisting of: 5' TAWRTT 3' (where R=A or G), 5' TAWGMT 3', and 5' TAARMT 3'.

4. An isolated DNA expression control sequence comprising: at least one lac operator sequence comprising the sequence 5' GTGAGCGGATAACAAT 3' (SEQ ID NO:3); a −30 region having a sequence represented by the sequence 5' TTGCTW 3' (where Y=C or T and W=A or T); and a −12 region having a sequence represented by a consensus sequence selected from the group consisting of: 5' TAWRTT 3' (where R=A or G), 5' TAWGMT 3' (where M=A or C), and 5'TAARMT 3'.

5. An isolated DNA expression control sequence comprising: at least one lac operator sequence comprising the sequence 5' GTGAGCGGATAACAAT 3' (SEQ ID NO:3); a −30 region having the sequence 5' TTGACT 3'; and a −12 region having the sequence 5' TAAGAT 3'.

6. An isolated DNA expression control sequence of claim 1 wherein said lac operator sequence begins at position −28.

7. An isolated DNA expression control sequence of claim 1 wherein said lac operator sequence begins between nucleotide positions +1 and +6.

8. An isolated DNA expression control sequence of claim 1 wherein the expression control sequence comprises two said lac operator sequences.

9. An isolated DNA expression control sequence of claim 8 wherein a first lac operator sequence 5' GTGAGCGGATAACAAT 3' (SEQ ID NO:3) is located at nucleotide position −28 and a second lac operator sequence 5' GTGAGCGGATAACAAT 3' (SEQ ID NO:3) is located downstream of the start of transcription.

10. An isolated DNA expression control sequence of claim 8 wherein said second lac operator sequence begins between nucleotide position +1 and +6.

11. An isolated DNA expression control sequence selected from the group consisting of: expression control sequence M (SEQ ID NO:4); expression control sequence M+D (SEQ ID NO:5); expression control sequence U+D (SEQ ID NO:6); expression control sequence M+D1 (SEQ ID NO:7); and expression control sequence M+D2 (SEQ ID NO: 8).

12. An expression vector comprising a DNA expression control sequence of claim 1.

13. The expression vector pHE4-0 (SEQ ID NO:10).

14. The expression vector pHE4a (SEQ ID NO:11).

15. A host cell comprising an expression vector of claim 12.

16. A method of producing a protein comprising:
(a) transforming a bacterium with an expression vector of claim 12, wherein the expression control sequence is operably linked to the coding sequence of a viral, prokaryotic, or eukaryotic protein, to form a recombinant cell;
(b) growing the cell such that the protein is expressed by the cell; and
(c) recovering the expressed protein.

17. The method of claim 16 wherein the bacterium is a member of a species selected from the group consisting of: E. coli, S. typhimurium, and B. subtilis.

18. A method of producing a protein comprising:
(a) inserting the expression vector of claim 12, wherein the expression control sequence of the vector is operably linked to the coding sequence of a desired viral, prokaryotic, or eukaryotic protein, into the chromosome of a bacterium to form a recombinant cell;
(b) growing the recombinant cell such that the protein is expressed by the cell; and
(c) recovering the expressed protein.

19. The method of claim 18 wherein the bacterium is a member of a species selected from the group consisting of: E. coli, S. typhimurium, and B. subtilis.

20. An expression vector comprising a DNA expression control sequence of claim 2.

21. A host cell comprising an expression vector of claim 20.

22. A method of producing a protein comprising:
(a) transforming a bacterium with an expression vector of claim 20, wherein the expression control sequence is operably linked to the coding sequence of a viral, prokaryotic, or eukaryotic protein, to form a recombinant cell;
(b) growing the cell such that the protein is expressed by the cell; and
(c) recovering the expressed protein.

23. The method of claim 22 wherein the bacterium is a member of a species selected from the group consisting of: E. coli, S. typhimurium, and B. subtilis.

24. A method of producing a protein comprising:
(a) inserting the expression vector of claim 20, wherein the expression control sequence of the vector is operably linked to the coding sequence of a desired viral, prokaryotic, or eukaryotic protein, into the chromosome of a bacterium, to form a recombinant cell;
(b) growing the recombinant cell such that the protein is expressed by the cell; and
(c) recovering the expressed protein.

25. The method of claim 24 wherein the bacterium is a member of a species selected from the group consisting of: E. coli, S. typhimurium, and B. subtilis.

26. An expression vector comprising a DNA expression control sequence of claim 3.

27. A host cell comprising an expression vector of claim 26.

28. A method of producing a protein comprising:
(a) transforming a bacterium with an expression vector of claim 26, wherein the expression control sequence is operably linked to the coding sequence of a viral, prokaryotic, or eukaryotic protein, to form a recombinant cell;
(b) growing the cell such that the protein is expressed by the cell; and
(c) recovering the expressed protein.

29. The method of claim 28 wherein the bacterium is a member of a species selected from the group consisting of: E. coli, S. typhimurium, and B. subtilis.

30. A method of producing a protein comprising:
(a) inserting the expression vector of claim 26, wherein the expression control sequence of the vector is operably linked to the coding sequence of a desired viral, prokaryotic, or eukaryotic protein, into the chromosome of a bacterium, to form a recombinant cell;
(b) growing the recombinant cell such that the protein is expressed by the cell; and
(c) recovering the expressed protein.

31. The method of claim 30 wherein the bacterium is a member of a species selected from the group consisting of: E. coli, S. typhimurium, and B. subtilis.

32. An expression vector comprising a DNA expression control sequence of claim 4.

33. A host cell comprising an expression vector of claim 32.

34. A method of producing a protein comprising:
(a) transforming a bacterium with an expression vector of claim 32, wherein the expression control sequence is operably linked to the coding sequence of a viral, prokaryotic, or eukaryotic protein, to form a recombinant cell;
(b) growing the cell such that the protein is expressed by the cell; and
(c) recovering the expressed protein.

35. The method of claim 34 wherein the bacterium is a member of a species selected from the group consisting of: E. coli, S. typhimurium, and B. subtilis.

36. A method of producing a protein comprising:
(a) inserting the expression vector of claim 32, wherein the expression control sequence of the vector is operably linked to the coding sequence of a desired viral, prokaryotic, or eukaryotic protein, into the chromosome of a bacterium, to form a recombinant cell;
(b) growing the recombinant cell such that the protein is expressed by the cell; and
(c) recovering the expressed protein.

37. The method of claim 36 wherein the bacterium is a member of a species selected from the group consisting of: *E. coli, S. typhimurium,* and *B. subtilis.*

38. An expression vector comprising a DNA expression control sequence of claim 5.

39. A host cell comprising an expression vector of claim 38.

40. A method of producing a protein comprising:
(a) transforming a bacterium with an expression vector of claim 38, wherein the expression control sequence is operably linked to the coding sequence of a viral, prokaryotic, or eukaryotic protein, to form a recombinant cell;
(b) growing the cell such that the protein is expressed by the cell; and
(c) recovering the expressed protein.

41. The method of claim 40 wherein the bacterium is a member of a species selected from the group consisting of: *E. coli, S. typhimurium,* and *B. subtilis.*

42. A method of producing a protein comprising:
(a) inserting the expression vector of claim 38, wherein the expression control sequence of the vector is operably linked to the coding sequence of a desired viral, prokaryotic, or eukaryotic protein, into the chromosome of a bacterium to form a recombinant cell;
(b) growing the recombinant cell such that the protein is expressed by the cell; and
(c) recovering the expressed protein.

43. The method of claim 42 wherein the bacterium is a member of a species selected from the group consisting of: *E. coli, S. typhimurium,* and *B. subtilis.*

\* \* \* \* \*